(12) United States Patent
Nakamura et al.

(10) Patent No.: US 8,981,947 B2
(45) Date of Patent: Mar. 17, 2015

(54) WATER QUALITY MONITORING APPARATUS

(75) Inventors: Kozaburo Nakamura, Osaka (JP); Prakash Sreedhar Murthy, Tsukuba (JP)

(73) Assignees: Mikasa Shoji Co., Ltd., Osaka (JP); Atonarp Inc., Tokyo (JP)

( * ) Notice: Subject to any disclaimer, the term of this patent is extended or adjusted under 35 U.S.C. 154(b) by 142 days.

(21) Appl. No.: 13/880,133

(22) PCT Filed: Oct. 18, 2011

(86) PCT No.: PCT/JP2011/005821
§ 371 (c)(1),
(2), (4) Date: Jul. 15, 2013

(87) PCT Pub. No.: WO2012/053193
PCT Pub. Date: Apr. 26, 2012

(65) Prior Publication Data
US 2013/0285821 A1    Oct. 31, 2013

(30) Foreign Application Priority Data

Oct. 18, 2010    (JP) .................... 2010-233561

(51) Int. Cl.
*G08B 21/00*    (2006.01)
*G08B 21/18*    (2006.01)
(Continued)

(52) U.S. Cl.
CPC ............ *G08B 21/182* (2013.01); *G01N 1/2273* (2013.01); *G01N 27/622* (2013.01); *G01N 33/18* (2013.01)
USPC ......... 340/603; 340/627; 73/53.01; 73/61.41; 210/85

(58) Field of Classification Search
CPC .................................................. G08B 21/182
USPC ......... 340/603, 606, 607, 612, 618, 627, 500, 340/540; 73/53.01, 863.01, 863.23, 61.41, 73/61.71; 324/442, 649, 694; 210/85, 210/96.2, 121, 187
See application file for complete search history.

(56) References Cited

U.S. PATENT DOCUMENTS 3,990,066 A * 11/1976 Malmgren .................... 340/603
7,391,333 B2 * 6/2008 Madden et al. ............... 340/603
(Continued)

FOREIGN PATENT DOCUMENTS

| JP | 03-258385 | 11/1991 |
| JP | 05-142119 | 6/1993 |

(Continued)

OTHER PUBLICATIONS

Joseph E. Roehl, A Microprocessor-Controlled Chemical Detection and Alarm System Based on Ion Mobility Spectrometry, IEEE Transactions on Industrial Electronics; May 1985; vol. 32, No. 2, pp. 108-113.

(Continued)

*Primary Examiner* — Anh V La
(74) *Attorney, Agent, or Firm* — Buchanan Ingersoll & Rooney PC

(57) ABSTRACT

There is provided a water quality monitoring apparatus including: an air quality analyzing unit detecting, using an ion mobility sensor, air quality in a space that is at least partially enclosed by a partition wall and a boundary surface with water whose water quality is to be monitored; and an alarm unit that outputs a signal indicating an abnormality if an air quality pattern obtained by the air quality analyzing unit is outside a tolerated range for air quality patterns of air that contacts the water to be monitored. Such water quality monitoring apparatus is capable of monitoring the water quality of drinking water inside a water tank or the like indirectly but precisely by detecting the quality of the air contacting the water using an ion mobility sensor.

16 Claims, 5 Drawing Sheets

(51) Int. Cl.
*G01N 1/22* (2006.01)
*G01N 27/62* (2006.01)
*G01N 33/18* (2006.01)

(56) References Cited

U.S. PATENT DOCUMENTS

2002/0130069 A1* 9/2002 Moskoff ......................... 210/85
2005/0247114 A1* 11/2005 Kahn et al. .................... 73/53.01
2007/0257684 A1* 11/2007 Essich ........................... 324/649
2008/0234948 A1 9/2008 Walk et al.

FOREIGN PATENT DOCUMENTS

| JP | 2000-146947 | 5/2000 |
| JP | 2000-292320 | 10/2000 |
| JP | 2001-083122 | 3/2001 |
| JP | 2009-002815 | 1/2009 |
| JP | 2009-500617 | 1/2009 |

OTHER PUBLICATIONS

J.I. Baumbach, "Process analysis using ion mobility spectrometry", Analytical and Bioanalytical Chemistry, Mar. 2006, vol. 384; No. 5, pp. 1059-1070.

International Preliminary Report on Patentability issued in corresponding International Application No. PCT/JP2011/005821.

* cited by examiner

WATER QUALITY MONITORING APPARATUS

TECHNICAL FIELD

The present invention relates to an apparatus for monitoring water quality.

BACKGROUND ART

Japanese Laid-Open Patent Publication No. 2004-74137 discloses the provision of a method and system for supplying drinking water monitored using aquatic organisms. The publication states that a bioassay system, which uses aquatic organisms supplied to monitor and judge hazardous substances such as acute poisons, is provided at a treatment stage from raw water to drinking water or on a water supply line. When the system judges that the results are acceptable, only treated water is preferentially supplied or clean water that can be used with the treated water is supplied together with the treated water. When the system judges that the results are not acceptable, only the clean water is automatically and independently supplied. To effectively operate such drinking water supplying system, only safe water is selectively transferred via safety-confirmation storage tanks that are used in emergencies and are installed on channels and/or treated water lines aside from clean water supply lines for municipal water or the like.

Japanese Laid-Open Patent Publication No. 2009-2815 discloses the provision of a monitoring apparatus with high selectivity that is a small-sized analyzer which dispenses with a vacuum system. Patent Document 2 discloses that two kinds of atmospheric pressure ion sources, namely, an atmospheric pressure ion source (non-dissociative atmospheric pressure ion source) for generating mainly molecular weight-related ions and an atmospheric pressure ion source (dissociative atmospheric pressure ion source) for generating mainly dissociated ions, are provided in an ion mobility spectrometer, with a mechanism for switching between the non-dissociative ion source and the dissociative ion source being further provided. Also provided is a database in which characteristic values (ion mobility or values related thereto) of the molecular weight-related ions generated by the non-dissociative ion source and the dissociated ions generated by the dissociative ion source are registered for each measurement target constituent. When ions that match the database are detected in both the non-dissociative ion source and the dissociative ion source modes, it is determined that a measurement target constituent has been detected. At such time, by also checking for the presence of dissociated ions during operation of the non-dissociative ion source and conversely for the presence of molecular weight-related ions during operation of the dissociative ion source and allowing such results to contribute to the determination, reliability is improved.

DISCLOSURE OF THE INVENTION

Water tanks for storing drinking water or potable water are installed so as to be spread out at a variety of locations, such as water towers in different regions and on the rooftops of buildings. Such water tanks individually carry the risk of contamination or deterioration in water quality due to some circumstances or cause. Accordingly, there is demand for a system capable of easily monitoring water quality in individual water tanks.

One aspect of the present invention is a water quality monitoring apparatus including: an air quality analyzing unit that detects, using an ion mobility sensor, air quality in a space or region that is at least partially enclosed by a partition wall and a boundary surface with water whose water quality is to be monitored; and an alarm unit that outputs a signal indicating an abnormality if an air quality pattern obtained by the air quality analyzing unit is outside a tolerated range (allowable range or acceptable range) for air quality patterns of air that contacts the water to be monitored.

Air (the atmosphere) in a space with a boundary surface with water, includes substances that reflect the water quality below the boundary surface, that is, the water surface. In addition, substances caused by the water below the water surface accumulate in a space that is substantially enclosed above the water surface. Such substances caused by the water include vaporized substances included in the water, substances released to the air from the water, and gases produced by some cause present in the water. The ion mobility sensor ionizes molecules in the air and outputs a spectrum based on the mobility of the ionized molecules. For this reason, in the water quality monitoring apparatus, by detecting the air quality in a space that contacts the water and is substantially or effectively enclosed, it is possible to measure substances (constituents) that are caused by the water and are included in the air quality of the enclosed space and thereby possible to judge from such measurement result the water quality below the water surface indirectly but with sufficient precision.

Another aspect of the present invention is a water quality monitoring method including the following steps:
1. Detecting air quality in a space that is at least partially enclosed by a boundary surface with water whose water quality is to be monitored and a partition wall using an ion mobility sensor.
2. Outputting an abnormality signal if an output pattern of the ion mobility sensor is outside a tolerated range for air quality patterns that contact the water to be monitored.

DETAIL DESCRIPTION

Figure 1:
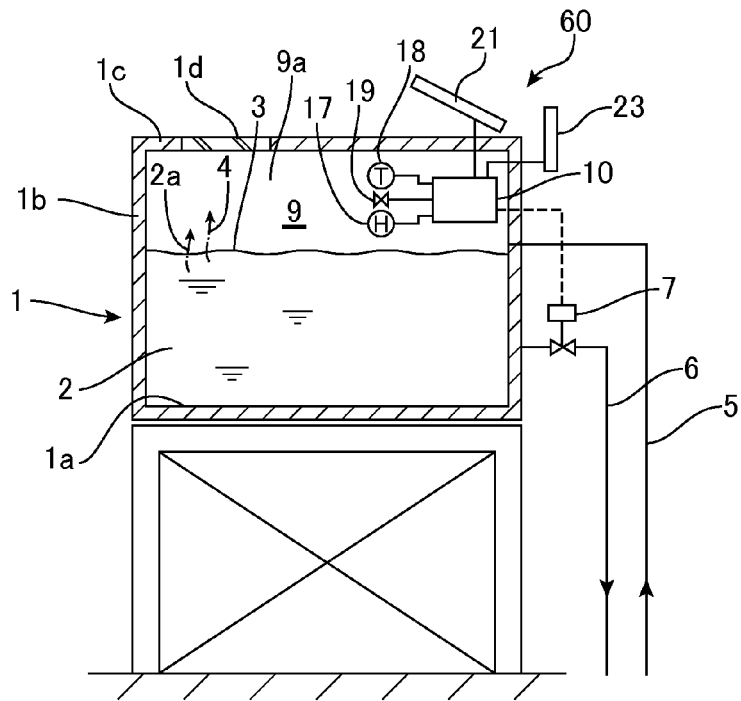
FIG. 1 shows an overview of a drinking water supplying apparatus including a water quality monitoring apparatus.
Figure 2:
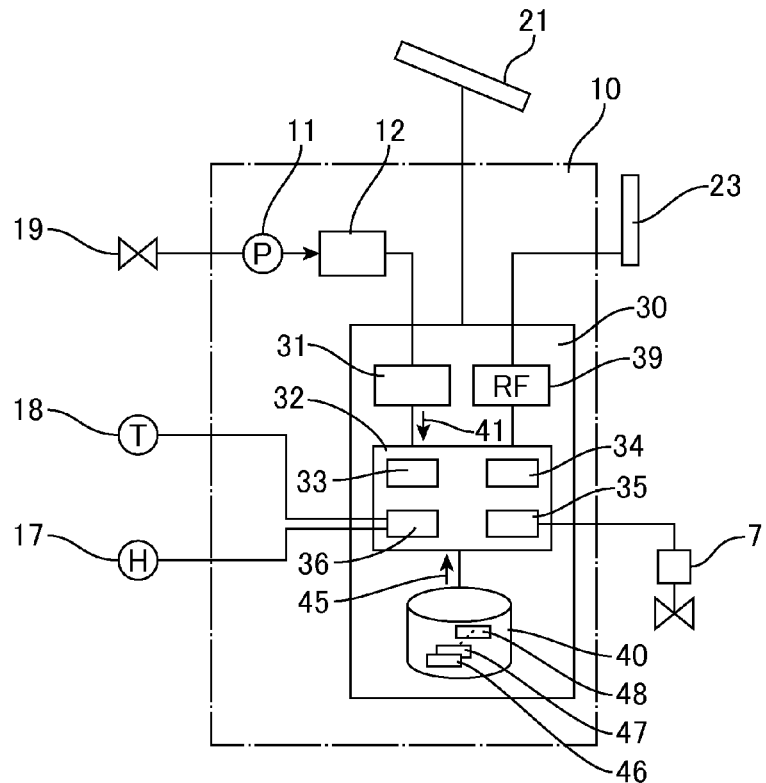
FIG. 2 is a block diagram of the water quality monitoring apparatus.

FIG. 1 shows how a water quality monitoring apparatus is attached to a water tank installed on the rooftop of a building or the like. FIG. 2 shows the overall construction of a water quality monitoring apparatus 10. The water quality monitoring apparatus 10 includes an air quality analyzing unit 31 that detects, using an ion mobility sensor 12, air quality in a space (or region) 9 that is at least partially enclosed by a boundary surface (water surface) 3 of the water 2 whose water quality is to be monitored and the wall(s) of a water tank 1 that act as partition wall(s) and an alarm unit 32 that outputs a signal indicating an abnormality if an air quality pattern obtained by the air quality analyzing unit 31 is outside a tolerated range of air quality patterns for air that contacts water to be monitored.

The water quality monitoring apparatus 10 that analyzes the air (sampling air) 9a in the space 9 that contacts the boundary surface 3 for the water 2 detects (measures) substances that are present in the sampling air 9a and reflect the water quality and is capable, from such measurement result, of judging the water quality below the water surface indirectly but with sufficient precision. Substances 4 caused by the water 2 below the water surface accumulate together with moisture (water vapor) in the space 9 that is effectively or substantially enclosed above the water surface. The substances (measurement target constituents) 4 present the air (sampling air) 9a in the space 9 due to the water include substances which are included in the water but have vaporized, such as VOCs like formaldehyde, geosmin (diosmin) which causes of moldy smells, chlorine, carbon tetrachloride, trihalomethane, and other carbon compounds. The measurement target constituents 4 also include substances (such as molecules, compositions, and compounds) released to the air from the water, such as cadmium, arsenic, hexavalent chromium, and cyanide compounds. The measurement target constituents 4 further include gases generated due to some cause in the water, such as gases (metabolized volatile substances) produced by the activity of *escherichia coli*, other bacteria, or microbes, and gases that accompany rotting or fermentation.

The ion mobility sensor 12 ionizes gas that has been introduced, for example molecules in the air, and outputs a spectrum based on the mobility of the ionized matter. Accordingly, by analyzing such spectrum, it is possible to distinguish or estimate the ionized substances included in the air. The water quality monitoring apparatus 10 detects measurement target constituents 4 included in the sampling air 9a by measuring the quality (air quality) of the sampling air 9a including substances in the air in the effectively enclosed space 9 that contacts the water using the ion mobility sensor 12 and analyzing the obtained or acquired spectrum (air quality pattern).

Accordingly, if measurement target constituents 4 that show that the water 2 is contaminated are included in the sampling air 9a obtained from the space 9 above the water surface, by analyzing the air quality pattern, the water quality monitoring apparatus 10 can determine an abnormality in the water quality at an early stage. Although the water 2 to be monitored is drinking water or potable water in this example, such water 2 may be industrial water, such as purified water, or wastewater (effluent), and in most cases water quality standards will exist for the water 2 to be monitored. The result of measuring air quality (an air quality pattern) of air that contacts water of a water quality corresponding to a tolerated water quality standard (an acceptable or an allowable water quality standard) is obtained in advance through experimentation or preliminary measurement. For this reason, even if every constituent included in an air quality pattern in which the presence of every ionizable molecule in the air 9a that contacts the water 2 is reflected is not identified, by comparing an obtained air quality pattern with air quality patterns that conform to water quality standards, it is possible to output an abnormality signal. Accordingly, it is possible to provide the water quality monitoring apparatus 10 that has a simple configuration but is high precise.

Substances aside from substances caused by the water 2 below the water surface are also included in the sampling air 9a of the space 9. As one example, if a compound, bacteria, decomposed matter, or the like that is capable of contaminating the water 2 is dropped into the space 9, measurement target constituents 4 caused by such are included in the sampling air 9a. Accordingly, by monitoring the sampling air 9a of the space 9 using the water quality monitoring apparatus 10, it is possible to monitor contamination of the water 2 at a much earlier stage.

One method of improving the detection precision (analysis precision) of the water quality monitoring apparatus 10 is to raise or increase the concentration of the measurement target constituents 4, or in other words, the chemical substances (chemical constituents, molecules, compositions, or compounds) to be measured by the ion mobility sensor 12 that are present inside the space 9 (i.e., in the sampling air 9a) that contacts the water. It is also possible to bubble the water 2 to be measured using a carrier gas (typically air) that supplies the sampling air 9a in the space 9 to the ion mobility sensor 12. Also, using a hollow fiber filter or the like, the constituents to be measured may be vaporized via pervaporation.

It is also effective for the water quality monitoring apparatus to include a vaporization unit that promotes vaporization of the water 2 to be monitored and a dehumidifier unit that dehumidifies the air in the space and supplies the air to the ion mobility sensor 12. By promoting the vaporization of water, it is possible to transfer the measurement target constituents 4 to the space together with the water vapor (moisture) 2a and raise the concentration of the measurement target constituents (measurement target components) 4 in the space. After this, by dehumidifying to reduce the moisture, it is possible to increase the concentration of the measurement target constituents 4 in the sampling air (carrier gas) 9a supplied to the ion mobility sensor 12.

The vaporization unit may include a unit that promotes vaporization using heat. If substances that vaporize or substances whose concentrations change at different temperatures are included in the water 2 to be monitored, the air quality pattern obtained by the ion mobility sensor 12 will change according to the temperature used to vaporize the water 2. Accordingly, it is possible to judge the water quality by associating information on the water temperature of the vaporization unit and air quality patterns. The vaporization unit may include an ink jet that sprays the water or ultrasonic vibration that mechanically vaporizes (atomizes) the water. It is also effective to vaporize water that hardly includes any impurities by dripping. On the other hand, when impurities that could cause clogging are included, mechanical vaporization using ultrasonic vibration or the like is effective.

The vaporization unit may be equipped with porous boundary walls that form the boundary surfaces. It is possible to use boundary walls of a porous ceramic, porous glass or a porous membrane. By passing water through or storing water in a vessel or pipe (tube) equipped with porous boundary walls, it is possible to easily expand the vaporization area in a limited space and thereby increase the concentration of the measurement target constituents included in the sampling air 9a.

It is desirable to supply the sampling air 9a where the concentration of moisture 2a together with the measurement target constituents 4 has increased via a dehumidifier unit to the ion mobility sensor 12. Since the air quality in the space becomes saturated with moisture or a state that is close to saturation, by dehumidifying using a method where it is difficult for other constituents to be adsorbed, it is possible to suppress the effect of the moisture spectrum on the air quality pattern, which makes higher precision monitoring possible. If the moisture peak becomes too large, the peaks of the measurement target constituents may be hidden or become difficult to detect. There is also the merit that it is possible to purge the ion mobility sensor 12 with dehumidified air.

Although the dehumidifier unit may be an adsorptive material such as silica gel or a molecular sieve, time and energy are consumed by regeneration. The dehumidifier unit may remove moisture by lowering relative humidity through heating or cooling with a Peltier element or the like. The dehumidifier unit may be equipped with hygroscopic boundary walls, for example, hygroscopic films such as Nafion (registered trademark) made by DuPont. By interposing a hygroscopic film between dry air and the sampling air 9a that includes lots of moisture, continuous dehumidification is possible.

It is also possible to increase the concentration of the measurement target constituents in the space 9 by returning and circulating the exhaust of the ion mobility sensor 12 that analyzes the sampling air 9a to the space 9. A unit that bubbles the exhaust of the ion mobility sensor 12 through the water 2 may also be provided. It is possible to increase the contained percentage of constituents that affect water quality at low concentrations in the sampling air 9a, which makes even more precise monitoring possible.

It is also effective for the water quality monitoring apparatus to include a reaction unit that samples the water 2 and supplies a product gas produced by causing a reaction with the water 2 sampled and a reagent to the ion mobility sensor 12. By replacing constituents that affect water quality at low concentrations and constituents that are difficult to ionize with other constituents that are easy for an ion mobility sensor to detect, it is possible to monitor with even higher precision.

It is also effective for the water quality monitoring apparatus to include a sampling unit that samples water from a plurality of different depths and forms a plurality of spaces 9. It becomes possible to monitor not only the water quality of water at the surface but also the water quality of water at a deep level.

As described below, one example of a water quality monitoring apparatus monitors water quality in a water tank. By installing a water quality monitoring apparatus at an appropriate location inside a water tank, it is possible to monitor not only the quality of the stored water but also the environment inside the water tank. It is also desirable to further include a transmission unit that transmits the output of an alarm unit to a manager (or managing organization) of the water tank. Such manager is capable of automatically monitoring water tanks at respective locations.

Another example of a water quality monitoring apparatus monitors water quality while floating on the water. A device that floats on water may have a position that is fixed using a buoy or the like or may monitor water quality while moving on a predetermined course using an autonomous movement mechanism such as a propeller or using an external movement mechanism. It is desirable for a moving water quality monitoring apparatus to include a unit for measuring the position, such as GPS, and to transmit water quality information associated with a position to the manager.

The alarm unit 32 is capable of outputting a warning signal if the air quality pattern obtained by the air quality analyzing unit 31 is not within a normal range even if such air quality pattern is in a tolerated or allowable range for air quality patterns above a water surface. By doing so, it is possible to monitor a stage prior to the water quality becoming abnormal. The alarm unit 32 may include a unit that changes the tolerated range according to an output of a sensor that measures environmental conditions, for example, temperature and humidity, inside the space. The sensitivity of the ion mobility sensor 12 can be affected by environmental conditions inside the space, such as temperature and humidity. Accordingly, by considering the environmental conditions inside the space, monitoring with even higher precision is possible.

It is desirable for such water quality monitoring apparatus to further include a unit for causing the water quality monitoring apparatus to float on the water surface. This makes it possible to omit the job of attaching the water quality monitoring apparatus. Since it is possible to suppress changes in the distance from the water surface to the ion mobility sensor, it is possible to monitor water quality with higher precision.

FIG. 1 shows an overview of a drinking water supplying apparatus 60 installed on the rooftop of a building or the like. The drinking water supplying apparatus 60 includes a water tank 1 (or "tank" or "reservoir tank") for storing drinking water 2. The reservoir tank 1 includes a bottom 1a, a side wall 1b, and a ceiling 1c that form the partition walls. The supplying apparatus 60 includes a pipe (filling pipe) 5 for supplying water to the reservoir tank 1, a pipe (water supply pipe) 6 that supplies water from the reservoir tank 1 to the user, and an emergency shutoff valve 7 that is attached to the water supply pipe 6 and stops the supplying of the drinking water 2. The supplying apparatus 60 includes the water quality monitoring apparatus 10 and the water quality monitoring apparatus 10 is disposed in the space (region) 9 surrounded by the water surface 3, the side wall 1b, and the ceiling 1c inside the water tank 1. The water quality monitoring apparatus 10 is typically attached above an overflow level of the side wall 1b of the water tank 1 or to the ceiling 1c. The space 9 inside the water tank 1 where the water quality monitoring apparatus 10 is attached is a space that is enclosed by the water surface 3 that is the boundary surface with the drinking water 2, the side wall 1b and the ceiling 1c, and although there are parts such as an overflow (not shown) and an inspection opening 1d that are open or can be opened to the outside, the space 9 is substantially or effectively an enclosed space.

The supplying apparatus 60 further includes a solar cell 21 that supplies power and is installed outside the water tank 1 and a communication antenna 23, with such components being connected to the water quality monitoring apparatus 10. The water quality monitoring apparatus 10 includes an interface that operates the emergency shutoff valve 7, with the water quality monitoring apparatus 10 shutting off the water supply pipe 6 on detecting an abnormality. The water quality monitoring apparatus 10 includes an opening 19 that draws in air from the space 9 inside the water tank 1, a temperature sensor 18 that detects the temperature inside the space 9, and a humidity sensor 17 that detects the humidity inside the space 9. The temperature sensor 18 and the humidity sensor 17 may be incorporated in the water quality monitoring apparatus 10 or may be installed at any location in the space 9.

FIG. 2 shows the overall configuration of the water quality monitoring apparatus 10 by way of a block diagram. The water quality monitoring apparatus 10 includes a pump (fan, blower) 11 that draws in air (sampling air) 9a from the space 9 inside the water tank 1, the ion mobility sensor 12 that detects the quality (air quality) of the drawn-in sampling air 9a, and a control unit 30 that drives the ion mobility sensor 12, analyzes the detection result of the ion mobility sensor 12, and carries out processing set in advance based on the analysis result. The ion mobility sensor (ion mobility spectrometer) 12 is a sensor that ionizes the substances (molecules) in air and outputs a spectrum (output pattern, air quality pattern) based on differences in mobility between the ionized substances. The water quality monitoring apparatus 10 includes an ion mobility sensor 12 called a FAIMS (Field Asymmetric Waveform Ion Mobility Spectrometer) or a DMS (Differential Mobility Spectrometer). A spectrometer (sensor, hereinafter referred to in general as "DMS") 12 of this type inputs ionized molecular flows into an asymmetrical electric field that changes from high voltage to low voltage and outputs the result of filtering such flows based on ion mobility in an electric field. A "microDMx" made by SIONEX and a FAIMS device made by OWLSTONE can be given as examples of compact DMS 12 that are commercially available.

In the DMS 12, a differential voltage (or "AC voltage", "electric field voltage Vrf", hereinafter simply "Vf") and a compensation voltage (or "DC voltage", hereinafter simply "Vc") that control the electric field are changed to alternately and asymmetrically switch between a high electric field and a low electric field. By doing so, during flight, chemical substances aside from target substances collide with the electrodes (plates) that generate the electric field so that plus ions and minus ions lose their electric charge and are not detected. On the other hand, if the conditions of the voltage Vf and the voltage Vc are appropriately controlled, ionized chemical substances that are the detection target can reach and be made to collide with a detector.

The control unit 30 is realized by a computer, a system LSI, an ASIC, or the like including a CPU and a memory. The control unit 30 includes a driver (air quality analyzing unit 31) that drives the DMS 12 according to conditions suited to detecting air quality in the sealed space 9, the alarm unit 32 that outputs an abnormality signal, a transmission unit 39 that transmits information from the alarm unit 32, and a memory 40. The alarm unit 32 outputs an abnormality signal if the air quality pattern 41 obtained by the air quality analyzing unit 31 is not in a tolerated range for air quality patterns of the space 9 above the water surface 3, that is, air quality patterns of air that contacts the water surface 3. The transmission unit 39 transmits the output of the alarm unit 32 via the antenna 23 to a manager of the drinking water supplying apparatus 60, for example, a water tank supplying company or a water tank management company. The memory 40 includes a database storing patterns 45 that are to be compared with the air quality pattern 41 obtained by the air quality analyzing unit 31. As one example, functions as the air quality analyzing unit 31, the alarm unit 32, and the transmission unit 39 are supplied as programs (program products) and are stored in the memory 40. A processor, such as the CPU of the control unit 30 downloads programs as appropriate to realize predetermined functions.

The transmission unit 39 is not limited to wireless communication and may be capable of communication with a building, a management company, or the like via a wired connection. The transmission unit 39 may be capable of communication using a communication system such as a mobile telephone network or a wireless LAN. The transmission unit 39 may be a transmission/reception unit and may be used to remotely monitor the water quality monitoring apparatus 10 and/or to update the patterns for comparison purposes stored in the database in the memory 40.

The alarm unit 32 includes a first function 33 that outputs an abnormality signal (red signal) if the obtained air quality pattern 41 is not in a range that is tolerated (allowable or permissible) as the air quality patterns for air above the water surface 3, a second function 34 that outputs a warning signal (yellow signal) if the obtained air quality pattern 41 is in a range that is tolerated (allowable or permissible) as the air quality patterns for air above the water surface 3 but is not in a normal range, a function 35 that carries out processing such as operating the emergency shutoff valve 7 when there is an abnormality signal, and a function 36 that selects and/or corrects the patterns 45 to be compared with obtained air quality pattern 41 in accordance with the temperature and humidity of the space 9 above the water surface 3.

The memory (database) 40 includes normal air quality patterns 46 obtained in a state in which normal air is contacting the surface of water of a suitable water quality as drinking water, precarious (caution needed) air quality patterns 47 obtained in a state in which air is contacting the surface of water that is drinkable but cannot be said to be optimal, and abnormal (dangerous) air quality patterns 48 obtained in a state where air contacts the surface of water of a water quality that is not drinkable. The precarious air quality patterns 47 also include air quality patterns that have an adverse effect on water quality and the abnormal air quality patterns 48 include air quality pattern that cause deterioration or make toxic the water quality of drinking water. The normal air quality patterns 46 include air quality patterns including vaporized constituents from drinking water that includes a suitable amount of chlorine or the like.

The precarious air quality patterns 47 include air quality patterns that include known vaporized constituents that indicate deterioration in water quality but cannot be said to be harmful in low concentrations, such as 2-methylisoborneol which can cause a moldy odor, diosmin (geosmin), and volatile organic compounds (VOCs).

The abnormal air quality patterns 48 include air quality patterns where the above constituents that indicate deterioration in water quality are included with a high concentration, and air quality patterns including hazardous substances such as explosives (like dimethyl-dinitrobutane that is a compound related to C-4, cyclohexane that is a compound related to RDX, and DNT and dinitrobenzene that are compounds related to TNT) and chemical weapons (like dibthyl sulfide and 2-chloroethyl that are compounds related to mustard gas and diisopropyl and methyl phosphonate that are compounds related to sarin). There is a constant threat of attacks using explosives, chemical substances, and/or biological substances. Accordingly, it is desirable to have an abnormality signal reliably outputted for known threats out of such threats.

In addition, the abnormal air quality patterns 48 include air quality patterns that include constituents that cause foul smells such as methane and ethane released from rotting matter. There is also the risk of animal or plant life becoming mixed in the water tank 1 for some reason, breeding, and then rotting as a corpse. Such situation is not favorable in maintaining the water quality of drinking water. Accordingly, it should preferably be possible to output an abnormality signal when such foul air is included in the space 9 of the water tank 1.

The abnormal air quality patterns 48 also include air quality patterns that include gas (metabolized volatile substances) released due to the activity of bacteria and microbes. In addition to the danger of biological weapons such as anthrax, water quality that includes a large amount of *E. coli* or the like is dangerous as drinking water. Accordingly, if metabolized volatile substances of known bacteria out of such bacteria are included in the air quality pattern 41 of the space 9 above the water surface 3, there will be the possibility of such threats being present in the water 2. Accordingly, it is preferable for an abnormality signal to be outputted reliably.

The DMS 12 ionizes the ionizable molecules in the air and outputs the air quality pattern 41 in which fundamentally all information on the ionized molecules is included. Accordingly, if molecules that cause the precarious or abnormal (dangerous) states described above or unknown molecules are included as the measurement target constituents 4 in the sampling air 9a, such molecules are ionized and the air quality pattern 41 including information relating to all of such ionized molecules is outputted. In addition, the space 9 is effectively sealed (enclosed) so that evaporant from the water surface 3 accumulates and becomes concentrated. For this reason, if a cause of a precarious or abnormal state is present in the water 2 and the space 9, the air quality pattern 41 obtained from the space 9 will differ to the normal air quality patterns 46. Accordingly, if the air quality pattern 41 differs to the normal air quality patterns 46, by setting such state as "precarious" or "abnormal", it is possible to precisely monitor water quality.

In this way, in the water quality monitoring apparatus 10, by obtaining the air quality pattern 41 for the space 9 above the water surface 3, it is possible to detect the water quality of the water 2 stored in the water tank 1 indirectly but with high precision and also possible to output an abnormality. By correcting the patterns 45 to be compared according to environmental conditions, such as the temperature and humidity of the space 9, and selecting a pattern suited to the environmental conditions from the database 40, it is possible to monitor the water quality of the water tank 1 with even higher precision.

A variety of pattern matching algorithms and pattern recognition algorithms for the air quality pattern 41 obtained from the DMS 12 and the patterns provided in the database 40 can be used. In the water quality monitoring apparatus 10, it is first determined whether the water quality is in a normal range and other states are determined to be abnormal and/or precarious. This means that in the water quality monitoring apparatus 10, identification of the respective constituents included in the air quality pattern 41 obtained by the DMS 12 is not carried out. Accordingly, processing, such as template matching, a neural network, statistical analysis, and a genetic algorithm, for identifying the respective constituents is unnecessary, and it is possible to monitor water quality at high speed using a simple mechanism.

The water quality monitoring apparatus 10 may be provided with an analysis unit (analysis function) that identifies measurement target constituents using a genetic algorithm or the like. It is possible for the analysis unit to identify the respective constituents included in the air quality pattern 41 obtained by the DMS 12 and determine the specific threat.

Figure 3:
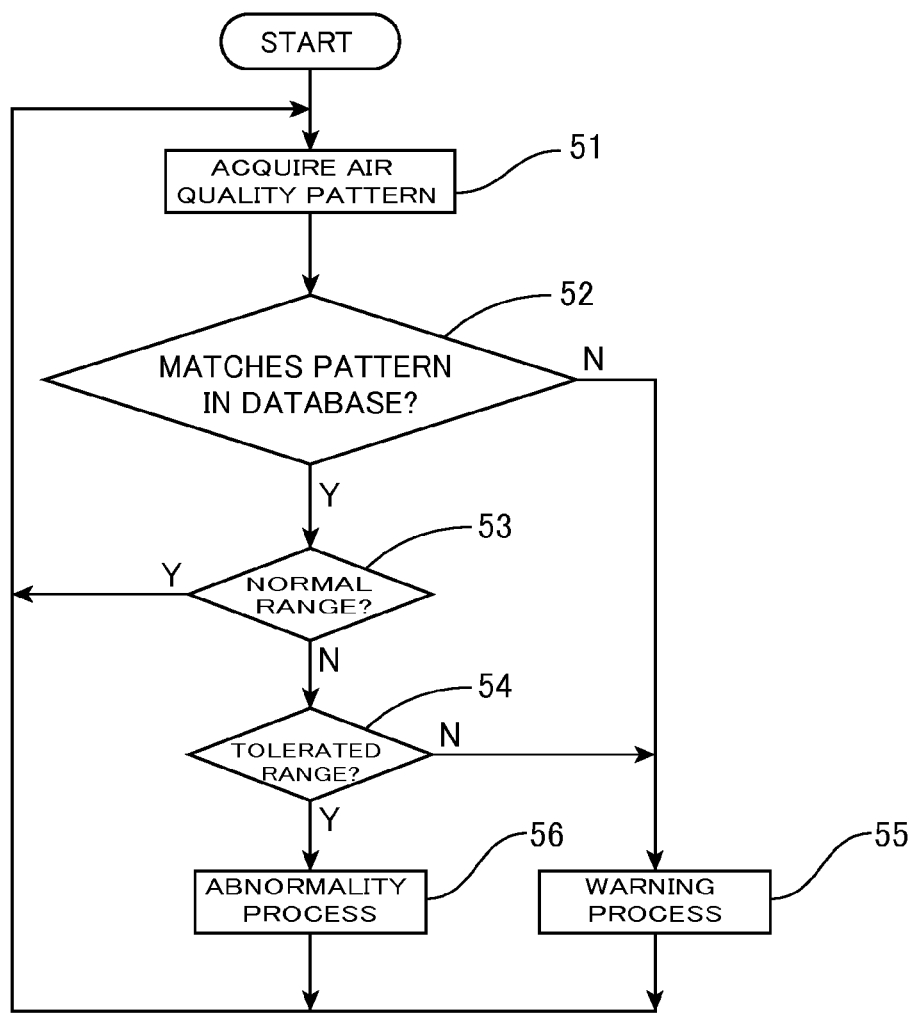
FIG. 3 is a flowchart showing control of the water quality monitoring apparatus.

FIG. 3 shows an overview of the processing by the water quality monitoring apparatus 10 by way of a flowchart. In step 51, the sampling air 9*a* of the space 9 enclosed above the water surface 3 is measured by the DMS 12 to acquire the air quality pattern 41 of the sampling air 9*a*. In step 52, the alarm unit 32 determines whether the obtained air quality pattern 41 matches or corresponds to one of the air quality patterns 46 to 48 provided in advance in the database 40 or a pattern produced by correcting such air quality patterns 46 to 48 according to temperature and humidity. If none of the patterns match, in step 55 the alarm unit 32 carries out abnormality processing for an abnormality in the water quality or an abnormality inside the water tank 1. The abnormality processing includes wireless transmission of an abnormality signal (red signal) via the RF unit 39 to a management company and/or closing the emergency shutoff valve 7. The determination of whether there is a corresponding or matching pattern includes a comparison of peak positions, heights, widths, and peak shifts included in the air quality pattern when the voltages Vf and Vc of the DMS 12 have been changed. Such determination includes a comparison with the air quality patterns 46 to 48 provided in advance, including changing the air quality pattern by changing the concentration of the measurement target constituents in the sampling air 9*a* as described below and/or controlling the temperature and humidity.

In step 53, if the obtained air quality pattern 41 corresponds to or matches the normal air quality patterns 46 provided in advance in the database 40 or a pattern produced by correcting the air quality patterns 46 in accordance with the temperature and humidity, the alarm unit 32 returns to step 51 and continues to monitor the water quality. In step 54, if the obtained air quality pattern 41 corresponds to or matches the precarious air quality patterns 47 provided in advance in the database 40 or a pattern produced by correcting the precarious air quality patterns 47 in accordance with the temperature and humidity, the alarm unit 32 carries out a warning process in step 56. The warning process includes wireless transmission of a warning signal (yellow signal) via the RF unit 39 to the management company.

In step 54, if the obtained air quality pattern 41 corresponds to or matches the abnormal air quality patterns 48 provided in advance in the database 40 or a pattern produced by correcting the abnormal air quality patterns 48 in accordance with the temperature and humidity, the alarm unit 32 carries out an abnormality process in step 55. By providing the abnormal air quality patterns 48 in the database 40, it is possible for the alarm unit 32 to determine that a known danger is present and if the known danger has been established, it is possible to actively carry out the abnormality processing.

Figure 4:
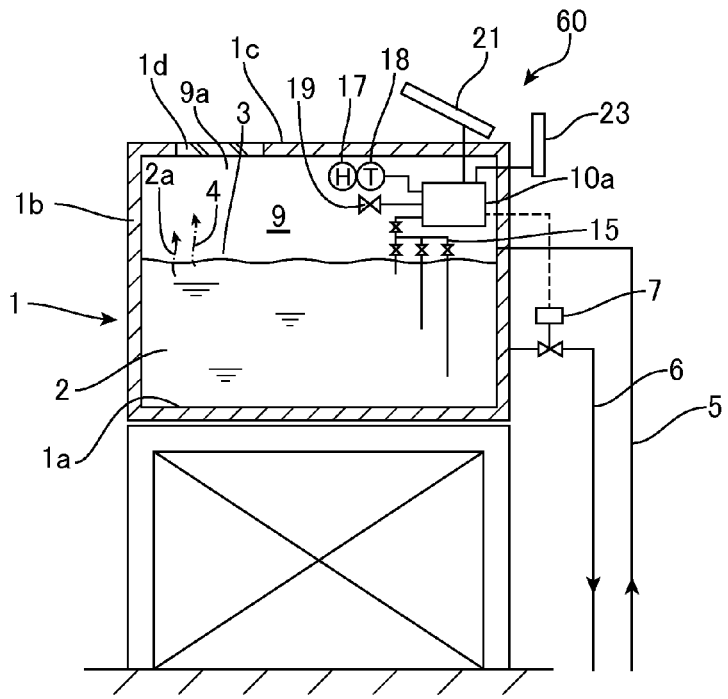
FIG. 4 shows an overview of a different drinking water supplying apparatus.
Figure 5:
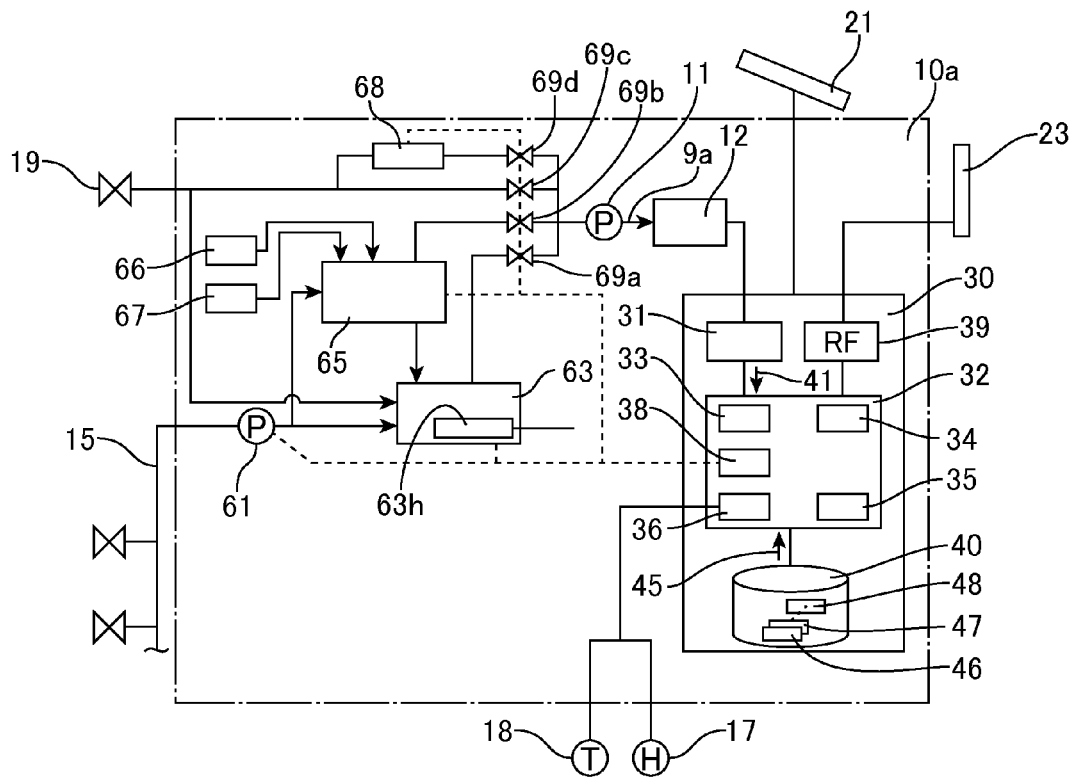
FIG. 5 is a block diagram of another water quality monitoring apparatus.

FIG. 4 shows a drinking water supplying apparatus 60 where a different water quality monitoring apparatus 10*a* is installed in the water tank 1. Also, FIG. 5 shows the overall configuration of the water quality monitoring apparatus 10*a* by way of a block diagram. The drinking water supplying apparatus 60 includes a sampling line (tube or pipe) 15 that samples water from an appropriate depth in the drinking water 2 below the water surface 3 and supplies the sample to the water quality monitoring apparatus 10*a*. As shown in FIG. 5, in addition to the DMS 12 and the control unit 30, the water quality monitoring apparatus 10*a* includes a pump 61 that samples the water 2 via the sampling line 15, a vaporization unit (vaporizer) 63 that forcibly vaporizes the sampled water 2 and supplies the vapor to the DMS 12, a reaction unit (reactor) 65 that supplies product gas resulting from the sampled water 2 reacting with reagents 66 and/or 67 to the DMS 12, a dehumidifier unit (dehumidifier) 68 that dehumidifies the air in the space according to a non-adsorption method and supplies the air to the DMS 12, and valves 69*a* to 69*d* that select the air supplied to the DMS 12. Note that components that are the same as the water quality monitoring apparatus 10 have been assigned the same reference numerals and description thereof is omitted.

By forcibly vaporizing the water 2, the vaporization unit 63 includes (mixes) impurities or gas of a low concentration included in the water 2 into the sampling air 9*a* supplied to the DMS 12. By doing so, it is possible to increase the influence on water quality in the air quality pattern 41 obtained by the DMS 12.

Purge and trap is known as a method of concentrating volatile substances in water. In this method, the sampled water is bubbled using an inert gas and volatile substances are collected in a trap tube. After this, the trap tube is heated to release the adsorbed constituents and thereby concentrate the volatile constituents included in the sampled water. One example of the vaporization unit 63 is a unit that bubbles the sampled water 2 with an appropriate gas, as one example the sampling air 9*a* itself drawn in from the space 9, in place of inert gas. Since the concentration of the measurement target constituents 4 in the sampling air 9*a* increases due to bubbling, it is possible to effectively reflect the constituents of the water 2 in the sampling air 9*a* supplied to the DMS 12. Accordingly, it is possible to determine the water quality more accurately. Air quality patterns for when the vaporization unit 63 operates may be provided in advance in the database 40 and the air quality pattern 41 obtained by the DMS 12 may be compared with such air quality patterns.

Another example of the vaporization unit 63 is a unit that atomizes the sampled water 2 by applying ultrasonic vibration. It is possible to gasify or atomize the constituents of the water 2 and mix such constituents into the air supplied to the DMS 12 without applying heat to the water 2 or adding another gas, which makes it possible to detect the constituents of the water 2 more precisely using the DMS 12.

Yet another example of the vaporization unit 63 is a unit that vaporizes the sampled water 2 by applying heat. By heating the sampled water 2 using a heater 63h or the like, it is possible to mix heat-produced evaporant from the water 2 in the air supplied to the DMS 12 and to detect the constituents of the water 2 more precisely using the DMS 12. It is also possible to continue heating after the water 2 has been vaporized so as to vaporize the evaporation residue or to oxidize and then vaporize the evaporation residue. Accordingly, it is possible to mix such evaporant or oxide from the vaporization unit 63 in the air supplied to the DMS 12 so that constituents contained in the water 2 can be detected much more precisely using the DMS 12.

The reaction unit 65 introduces reagents 66 and/or 67 with a controlled amount and concentration into the water 2 to cause a reaction with the constituents mixed into the water 2 and mixes the produced gas into the air supplied to the DMS 12. By comparing the air quality pattern 41 obtained by the DMS 12 with patterns including constituents, concentrations, and amounts of the reagents 66 and 67 and/or products (product gases) established (measured) in advance, it is possible to determine the water quality of the water 2 more accurately. If the water 2 is not drinking water and is waste water or the like which is strongly acidic or strongly alkaline, the water 2 is neutralized using a suitable reagent and the evaporant from the neutralized water 2 may be detected by the DMS 12. The water 2 that has been caused to react with the reagents by the reaction unit 65 may be supplied to the vaporization unit 63 and supplied to the DMS 12 after forcible vaporization.

The dehumidifier unit 68 dehumidifies the sampling air 9a drawn in from the space 9 above the water surface 3 and supplies the dehumidified sampling air 9a to the DMS 12. If an adsorption-type dehumidifier apparatus is used, there is the possibility of fine constituents included in the sampling air 9a becoming adsorbed together with the moisture 2a. Accordingly, it is desirable for the dehumidifier unit 68 to use a non-adsorption method. One example of a non-adsorption method is to heat the air using a heater to lower the relative humidity. Another example of a simple non-adsorption method is a method that dehumidifies by cooling the air using a Peltier element and then heats with a heater to obtain a constant dryness.

By dehumidifying the sampling air 9a of the space 9 above the water surface 3 and supplying the sampling air 9a to the DMS 12, if measurement target constituents 4 whose peaks coincide with the moisture 2a in an air quality pattern are included in the sampling air 9a, there will be higher probability that such measurement target constituents 4 can be distinguished. By detecting air with different humidity using the DMS 12, from the drift in peaks included in the air quality pattern 41 due to the differences in humidity, it is possible to determine water quality more precisely and/or to obtain supplemental information for identifying the measurement target constituents 4 included in the water 2 or the sampling air 9a. By obtaining dehumidified air, it is also possible to regularly purge the DMS 12 and obtain stabilized performance over a long period.

The alarm unit 32 of the water quality monitoring apparatus 10a includes a mode control unit 38 that controls the operating states of the vaporization unit 63, the reaction unit 65, and the dehumidifier unit 68 described above and whether to mix the outputs (gasses) of such units 63, 65, and 68 into the air supplied to the DMS 12. The mode control unit 38 further includes a function that selects patterns to be compared with the air quality pattern 41 measured by the DMS 12 from the database 40. Passing through the vaporization unit 63, the reaction unit 65 or the dehumidifier unit 68 will probably causes the constituents included in the sampling air 9a obtained from the enclosed space 9 change. That is, the air quality pattern 41 of air (gas) outputted from the vaporization unit 63, the reaction unit 65, and the dehumidifier unit 68 or of sampling air 9a into which such air has been mixed will often differ to the air quality pattern of the sampling air 9a directly drawn in from the space 9. Accordingly, it is effective to provide patterns for comparing with such air quality pattern in the database 40.

Figure 6:
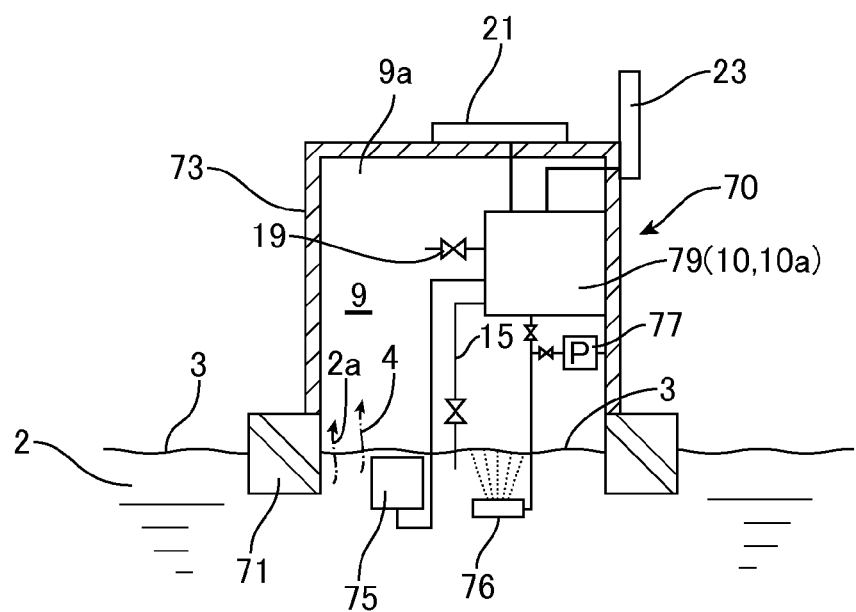
FIG. 6 shows an overview of a floating water quality monitoring apparatus.

FIG. 6 shows yet another water quality monitoring apparatus. Such water quality monitoring apparatus 70 is a type that floats on the water surface 3 and includes a float ring (float) 71 for providing buoyancy to keep the entire water quality monitoring apparatus 70 above the water and a partition wall (shell) 73 made of metal or plastic or the like that covers the water surface 3. The water quality monitoring apparatus 70 includes a monitoring unit 79 equipped with the functions of the water quality monitoring apparatus 10 or 10a described above. The monitoring unit 79 is installed inside the shell 73 and draws in sampling air 9a from the space 9 that is enclosed by the water surface 3 and the shell 73. Accordingly, the water quality monitoring apparatus 70 determines the water quality of the water 2 on which the water quality monitoring apparatus 70 is floating. Since the water quality monitoring apparatus 70 floats on the water surface 3, it is possible to keep the distance from the water surface 3 to the intake opening 19 substantially constant and to safely position the intake opening 19 closer to the water surface 3. This means it is possible to judge the water quality in a shorter time.

The water quality monitoring apparatus 70 includes a vaporization unit (vaporizer) 75 suspended below the water surface. The vaporization unit 75 forcibly vaporizes the water 2 in the region or space 9 inside the shell 73. A typical vaporization unit 75 is an ultrasonic vibrator or a heating element such as a heater. The vaporization unit 75 is kept at a constant distance (depth) from the water surface 3. This means that it is possible to supply moisture 2a efficiently to the space 9 and to also supply the measurement target constituents 4 to the inside of the shell 73 so as to accumulate and concentrate the measurement target constituents 4 that reflect the water quality in the space 9 inside the shell 73.

The water quality monitoring apparatus 70 also includes a bubbling unit 76 that is suspended below the water surface. Outside air is supplied to the bubbling unit 76 by a blower or air pump 77 and air that has been bubbled is supplied to the internal space 9 of the shell 73. The sampling air 9a is supplied from the internal space 9 to the DMS (ion mobility sensor) 12 of the monitoring unit 79. The ion mobility sensor 12 needs a certain amount of gas to constantly flow, including a flow as a carrier gas that transports the measurement target constituents 4 to the sensor 12. To do so, external air may simply be introduced into the internal space 9. However, there is the possibility that the concentration of the measurement target constituents in the internal space 9 will not become sufficiently high. By supplying bubbled external air to the internal space 9, it is possible to increase the concentration of the measurement target constituents in the space 9.

It is possible to circulate the exhaust of the DMS 12 included in the monitoring unit 79 to the internal space 9 or to circulate via the bubbling unit 76 to the internal space 9. This makes it possible to raise the concentration of the measurement target constituents in the internal space 9. On the other hand, there is the possibility that it will become difficult to reflect changes in the water quality below the water surface 3 in the sampling air 9a obtained from the internal space 9. Accordingly, it is desirable to regularly replace the internal space 9 with outside air (fresh air) or to appropriately control the proportions of exhaust (return air) of the DMS 12 and fresh air.

Since the water quality monitoring apparatus 70 is a type that floats on the water surface 3, it is possible to omit the job of attachment to the inner wall of the water tank 1. Also, by attaching to an appropriate anchor, it is possible to float the water quality monitoring apparatus 70 on running water and thereby monitor the water quality of running water (stream). Accordingly, this is also suited to monitoring water quality at an outlet or outflow of a wastewater treatment system.

Figure 7:
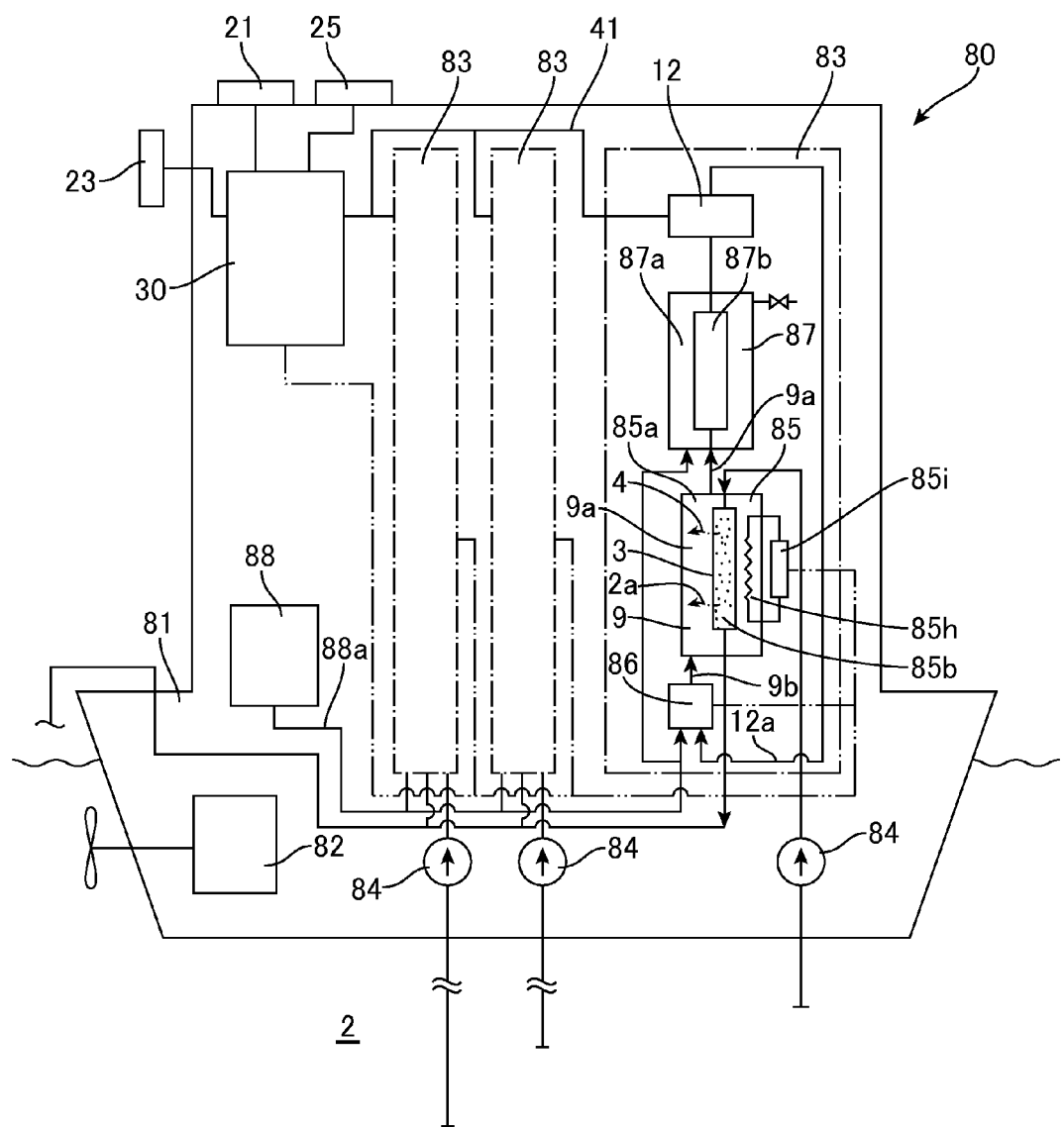
FIG. 7 shows an overview of a boat-type water quality monitoring apparatus.

FIG. 7 shows yet another water quality monitoring apparatus. This water quality monitoring apparatus 80 is a type that moves above the water 2 and includes a hull 81 that moves the water quality monitoring apparatus 80 on the water and an engine 82 for moving on the water. The water quality monitoring apparatus 80 includes three water analyzing units 83, three sampling pumps 84, a supply source 88 of dry air 88a, and the control unit 30. The control unit 30 has the same functions as the control unit 30 of the water quality monitoring apparatus 10 or 10a described above. The three water analyzing units 83 have the same construction and the respective water analyzing units 83 collect and analyze water 2 at different depths using the sampling pumps 84.

The respective water analyzing units 83 include a vaporization unit 85 that vaporizes the collected water 2 to produce the sampling air 9a, a gas supplying unit 86 that supplies the carrier gas 9b to the vaporization unit 85, a dehumidifying unit 87 that dehumidifies the sampling air 9a, and a DMS (ion mobility sensor) 12 that measures the measurement target constituents included in the dehumidified sampling air 9a. The dry air 88a that is fresh air and exhaust air 12a of the ion mobility sensor 12 that are return air are supplied to the gas supplying unit 86, the gas supplying unit 86 is equipped with a function for selecting the dry air 88a and the DMS exhaust 12a and a function for adjusting the mixing ratio of the respective gases. By supplying the DMS exhaust 12a to the vaporization unit 85, it is possible to produce sampling air 9a with a high concentration of measurement target constituents 4 and to monitor the water quality with high precision. By supplying fresh dry air 88a to the vaporization unit 85, it is possible to monitor water quality in real time.

The control unit 30 includes a function for controlling switching and the mixing ratio of the gas supplying unit 86, and controls the conditions of the carrier gas supplied to the vaporization unit 85 according to a schedule set in advance, the results obtained by the water analyzing units 83, or the like.

The vaporization unit 85 includes a chamber 85a and a vaporization tube 85b equipped with a porous circumferential wall (boundary wall) that is enclosed inside the chamber 85a. The water 2 collected by the sampling pump 84 is supplied to the vaporization tube 85b and the measurement target constituents 4 included in the water 2 are released via the vaporization tube 85b to the space 9 inside the chamber 85a with the moisture 2a. Accordingly, the surface of the vaporization tube 85b is the boundary surface 3 for the water 2 and the space 9.

Examples of the vaporization tube 85b include a porous glass tube, a porous ceramic tube, and a hollow fiber filter with many pores of a suitable pore diameter. By adjusting the length (pipe length) and diameter of the vaporization tube 85b, the water 2 is vaporized relative to the volume of the space 9 in the chamber 85a and it is possible to increase the area that releases the measurement target constituents 4 included in the water 2. Accordingly, it is possible to increase the concentration of the measurement target constituents 4 included in the sampling air 9a of the space 9.

The vaporization unit 85 includes a heater 85h that controls the temperature of the inside of the chamber 85a or the temperature of the vaporization tube 85b and a heater control unit 85i that controls the heater 85h. In the chamber 85a, it is possible to control the temperature at which the moisture 2a is formed and the measurement target constituents 4 are vaporized or released. By using the vaporization tube 85b, it is possible to form a wide vaporization area in the chamber 85a that has a small capacity and possible to reduce the area controlled by the heater 85h. Accordingly, it is easy to control the vaporization temperature (vaporization conditions) of the vaporization unit 85. By changing the temperature of the vaporization unit 85, it is possible to change the constituents released from the water 2 and possible for the ion mobility sensor 12 to grasp such changes in constituents. The water 2 may be continuously supplied by the sampling pump 84 to the vaporization tube 85b. It is possible to temporarily hold the water 2 in the vaporization tube 85b, to change the vaporization conditions such as the vaporization temperature inside the chamber 85a over time, and to measure the changes in the measurement target constituents 4 released inside the chamber 85a using the DMS 12. The water 2 that has passed the vaporization tube 85a is expelled in the aft direction so as to not affect the sampling of the water 2.

The dehumidifier unit 87 that dehumidifies the sampling air 9a includes a chamber 87a to which the dry air 88a is supplied and a dehumidifier tube 87b installed inside the chamber 87a. The dehumidifier tube 87b includes an adsorptive circumferential wall (boundary wall) and by passing the sampling air 9a through the dehumidifier tube 87b, moisture in the sampling air 9a is emitted to the outside dry air 88a via the adsorptive circumferential wall of the dehumidifier tube 87b. As a result, the moisture in the sampling air 9a is removed. Contrary, the sampling air 9a may pass to the chamber 87a and the dry air 88a may pass to the dehumidifier tube 87b.

One example of the dehumidifier tube 87b is a tube (pipe) made from Nafion (registered trademark) manufactured by DuPont. Such tube is capable of selectively removing the moisture 2a included in the sampling air 9a and suppressing a drop in the concentration of the measurement target constituents 4 in the sampling air 9a due to the measurement target constituents 4 being removed together with the moisture 2a. Since it is possible that some constituents will be removed together with the moisture 2a, it is effective to also use a dehumidifier of another method such as a Peltier element and to switch according to time division.

The dehumidified sampling air 9a is supplied to the DMS 12 and the air quality pattern 41 of the sampling air 9a is obtained. The air quality patterns 41 of the respective water analyzing units 83 are supplied to the control unit 30 and the water quality at the respective depths is judged. Such water quality monitoring apparatus 80 includes a GPS unit 25 and is capable of measuring its own position. Accordingly, the water quality monitoring apparatus 80 transmits the position where water quality was monitored together with the water quality at the respective depths to a monitoring center or the like.

The control unit 30 includes a function as a robot that monitors the water quality while moving on a lake surface or a sea surface in accordance with a predetermined route based on the position measured by the GPS unit 25. This means that it is possible to monitor the water quality in a wide body of water such as a lake or a bay using the water quality monitoring apparatus 80. Also, by using the water quality monitoring apparatus 80, it is possible to monitor the water quality inside or in the periphery of aquaculture pens.

Note that such water quality monitoring apparatuses 10, 10a, 70, and 80 are mere examples. The ion mobility sensor 12 of the water quality monitoring apparatus may be a sensor system that is connected to another type of sensor or the same or a different type of DMS. For example, it is possible to combine with gas chromatography (GC). The ion mobility sensor 12 is not limited to a DMS and may be another type of IMS, such as a TOFIMS, FTIR, or a combination of such DMS. The water quality monitoring apparatus may be equipped with another sensor that detects water quality, as one example, a pH monitor, a turbidimeter, or a radiation measurement unit.

Also, as described above, although the present invention has mainly been described using a water quality monitoring apparatus that monitors the water quality of drinking water as an example, the water to be monitored is not limited to drinking water and may be wastewater, effluent, river water, sea water, pure water, ultra-pure water, or the like.

The invention claimed is:

1. A water quality monitoring apparatus comprising:
   an air quality analyzing unit that detects, using an ion mobility sensor, air quality in a space that is at least partially enclosed by a partition wall and a boundary surface with water whose water quality is to be monitored; and
   an alarm unit that compares an air quality pattern that is obtained by the air quality analyzing unit and is an air quality pattern fundamentally including information on every constituent capable of being ionized and being detected by the ion mobility sensor, with a normal air quality pattern that is produced in a case where the ion mobility sensor measures air contacting water to be monitored when the water to be monitored is normal, without identifying the constituents included in the obtained air quality pattern, and outputs a signal indicating an abnormality if the obtained air quality pattern is outside a tolerated range for air quality patterns of air that contacts the water to be monitored.

2. The water quality monitoring apparatus according to claim 1, further comprising:
   a vaporization unit that promotes vaporization of the water to be monitored; and
   a dehumidifier unit that dehumidifies air in the space and supplies the air to the ion mobility sensor.

3. The water quality monitoring apparatus according to claim 2,
   wherein the vaporization unit includes a porous partition wall that forms the boundary surface.

4. The water quality monitoring apparatus according to claim 2,
   wherein the dehumidifier unit includes a hygroscopic boundary wall.

5. The water quality monitoring apparatus according to claim 1,
   further comprising a circulation unit that returns an exhaust of the ion mobility sensor to the space.

6. The water quality monitoring apparatus according to claim 5,
   wherein the circulation unit includes a unit that bubbles the water using the exhaust.

7. The water quality monitoring apparatus according to claim 1,
   further comprising a reaction unit that supplies a product gas produced by causing the water to be monitored to react with a reagent to the ion mobility sensor.

8. The water quality monitoring apparatus according to claim 1,
   further comprising a sampling unit that samples water at a plurality of different depths and forms a plurality of spaces.

9. The water quality monitoring apparatus according to claim 1,
   wherein the space is inside a water tank that stores the water to be monitored.

10. The water quality monitoring apparatus according to claim 1,
    further comprising a unit that causes the water quality monitoring apparatus to float on water.

11. The water quality monitoring apparatus according to claim 1,
    further comprising a transmission unit that transmits an output of the alarm unit to a manager of the water to be monitored.

12. The water quality monitoring apparatus according to claim 11,
    further comprising a positioning unit that detects a position of the water quality monitoring apparatus,
    wherein the transmission unit transmits the output including position information of the water quality monitoring apparatus.

13. The water quality monitoring apparatus according to claim 1,
    wherein the alarm unit outputs a warning signal if the air quality pattern obtained by the water quality monitoring apparatus is within a tolerated range for air quality patterns that contact the water but is outside a normal range.

14. The water quality monitoring apparatus according to claim 1,
    wherein the alarm unit includes a unit that changes the tolerated range according to an output of a sensor that measures environmental conditions inside the space.

15. A water quality monitoring method comprising:
    detecting, using an ion mobility sensor, air quality in a space that is at least partially enclosed by a boundary surface with water whose water quality is to be monitored and a partition wall; and
    comparing an output pattern of the ion mobility sensor, which fundamentally includes information on every constituent capable of being ionized and being detected by the ion mobility sensor, with a normal air quality pattern that is produced in a case where the ion mobility sensor measures air contacting water to be monitored when the water to be monitored is normal, without identifying the constituents included in the obtained output pattern, and outputting an abnormality signal if the obtained output pattern is outside a tolerated range for air quality patterns of air that contacts the water to be monitored.

16. The water quality monitoring method according to claim 15,
    further comprising outputting a warning signal if the output pattern is within a tolerated range for air quality patterns that contact the water but is outside a normal range.

* * * * *